(12) United States Patent
Mane et al.

(10) Patent No.: US 8,349,790 B2
(45) Date of Patent: Jan. 8, 2013

(54) SUBSTITUTED OCTANE(ENE) NITRILES, METHODS FOR THE SYNTHESIS THEREOF AND USES THEREOF IN PERFUMERY

(75) Inventors: Jean Mane, Grasse (FR); Jean-Claude Clinet, Villeneuve-Loubet (FR)

(73) Assignee: V. Mane Fils, Bar sur Loup (FR)

( * ) Notice: Subject to any disclaimer, the term of this patent is extended or adjusted under 35 U.S.C. 154(b) by 0 days.

(21) Appl. No.: 12/740,414

(22) PCT Filed: Oct. 28, 2008

(86) PCT No.: PCT/FR2008/051939
§ 371 (c)(1),
(2), (4) Date: Jul. 12, 2010

(87) PCT Pub. No.: WO2009/056756
PCT Pub. Date: May 7, 2009

(65) Prior Publication Data
US 2010/0279917 A1    Nov. 4, 2010

(30) Foreign Application Priority Data
Oct. 29, 2007   (FR) ...................................... 07 07587

(51) Int. Cl.
*A61Q 13/00*    (2006.01)
(52) U.S. Cl. ............................................... 512/6; 512/1

(58) Field of Classification Search ................... 512/1, 6
See application file for complete search history.

(56) References Cited

U.S. PATENT DOCUMENTS

| 3,655,722 A | * | 4/1972 | Mitchell et al. ............... 558/462 |
| 4,863,631 A | | 9/1989 | Sprecker et al. |
| 2008/0118443 A1 | | 5/2008 | Jaunky et al. |

* cited by examiner

*Primary Examiner* — Kuo-Liang Peng
(74) *Attorney, Agent, or Firm* — B. Aaron Schulman, Esq.; Stites & Harbison, PLLC

(57) ABSTRACT

Compounds of general formula (I) below:

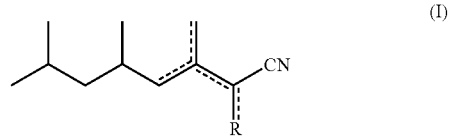

(I)

in which R is a hydrogen atom, a methyl group, a CH2OH group, an ester group, preferably COOEt, or a methylene group, and in which not more than one of the four dashed lines represents a carbon-carbon double bond, and also their enantiomers and their diastereoisomers,
a process for preparing them, and their use as an odorant agent in perfuming compositions.

18 Claims, No Drawings

SUBSTITUTED OCTANE(ENE) NITRILES, METHODS FOR THE SYNTHESIS THEREOF AND USES THEREOF IN PERFUMERY

The present invention relates to the field of fragrances, and pertains in particular to the preparation of new compounds, the process of synthesizing them, and their use in perfumery by virtue of their odorant properties. The compounds of the invention are 3,5,7-trimethyloctane(ene) nitriles and their α-substituted derivatives, and the use of these compounds in perfumery particularly as a raw material. The present invention also relates to perfumes and perfumed products comprising said compounds.

Many nitriles, aliphatic or aromatic, are presently used in the art of perfumery. They have been developed both for their high stability in aggressive media and for the fact of their frequent olfactory similarity with the corresponding aldehydes, the latter having been used in perfumery well before the development of the nitriles.

The Applicant has identified that certain 3,5,7-trimethyloctane(ene) nitriles and their derivatives bearing a substituent in the α position to the nitrile group, of general formula (I) shown below, possess a real advantage as a fragrance or perfume or as a raw material for perfumes or perfumed compositions. Not only are the compounds of the invention novel in the art of perfumery, but also, as far as the Applicant is aware, they have never been reported as such in the literature. The perfume industry is increasingly subject to regulations, and is looking for compounds which may replace or take on the identity of certain compounds whose use has recently been banned for reasons of safety or toxicity.

The invention provides in particular the compounds of general formula (I) below:

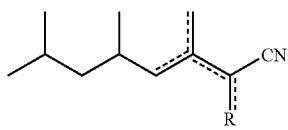

(I)

in which R is a hydrogen atom, a methyl group or a methylene group, and in which not more than one of the four dashed lines represents a carbon-carbon double bond.

According to one particular embodiment of the invention, the main chain is saturated and R represents a hydrogen atom, a methyl group or a methylene group.

According to another preferred embodiment, the compound according to the invention conforms to the formula (II) below:

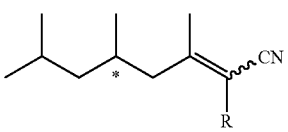

(II)

in which R is a hydrogen atom or a methyl group.

According to another preferred embodiment, the compound according to the invention conforms to the formula (III) below:

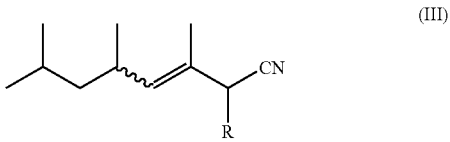

(III)

in which R is a hydrogen atom or a methyl group.

According to another preferred embodiment, the compound according to the invention conforms to the formula (IV) below:

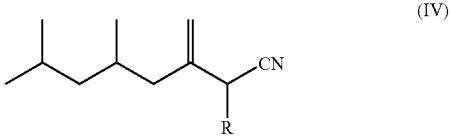

(IV)

in which R is a hydrogen atom or a methyl group.

According to another preferred embodiment, the compound according to the invention conforms to the formula (V) below:

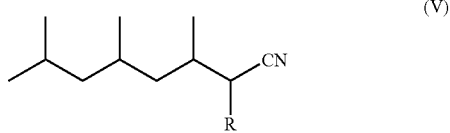

(V)

in which R is a hydrogen atom or a methyl group.

According to another preferred embodiment, the compound according to the invention conforms to the formula (VI) below:

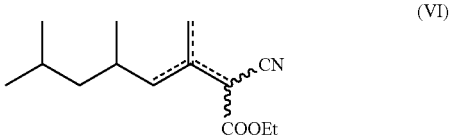

(VI)

According to another preferred embodiment, the compound according to the invention conforms to the formula (VII) below:

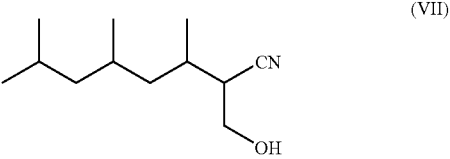

(VII)

According to another preferred embodiment, the compound according to the invention conforms to the formula (VIII) below:

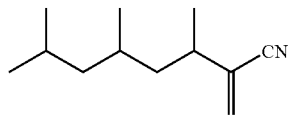
(VIII)

According to another preferred embodiment, the compound according to the invention conforms to the formula (IX) below:

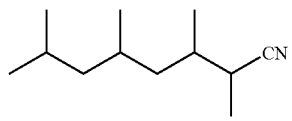
(IX)

The compounds according to the invention comprise one or more asymmetric carbons and, consequently, may take the form of mixtures of optical isomers, more particularly of enantiomers and of diastereoisomers. The present invention intends to protect compositions comprising at least one compound of general formula (I), in the form of an isomer or mixture of isomers, in particular of an enantiomer or mixture of enantiomers, or of a racemic mixture, or of a diastereoisomer or mixture of diastereoisomers. The invention accordingly also provides for the use of the compounds of general formula (I) as odorant agents.

The invention accordingly provides a composition characterized in that it comprises at least one compound according to the invention in the form of an isomer or mixture of isomers, an enantiomer or mixture of enantiomers, or a racemic mixture, or a diastereoisomer or mixture of diastereoisomers. According to one preferred embodiment, the composition according to the invention comprises a mixture of compounds of formula (II), (III), and (IV) as defined above. According to another embodiment of the invention, the composition comprises at least one of the two Z and E isomers of the compound (II) as defined above, or a mixture of said two isomers. According to yet another preferred embodiment, the composition comprises at least one of the four diastereoisomers of the compound (V) as defined above, or a mixture of said four diastereoisomers.

The invention also provides a composition comprising a mixture of two Z/E isomers of at least one compound of formula (II), (III) and/or (IV).

Since the compounds of the invention have at least one asymmetric carbon, the invention also provides a composition comprising a mixture of enantiomers or diastereoisomers of the compound (I); the invention also provides a composition comprising a mixture of enantiomers of the compound (II); the invention also provides a composition comprising a mixture of enantiomers or diastereoisomers of the compound (III); the invention also provides a composition comprising a mixture of enantiomers or diastereoisomers of the compound (IV); the invention also provides a composition comprising a mixture of enantiomers or diastereoisomers of the compound (V); the invention also provides a composition comprising a mixture of enantiomers or diastereoisomers of the compound (VIII); the invention also provides a composition comprising a mixture of enantiomers or diastereoisomers of the compound (IX).

The invention also provides a composition comprising a single enantiomer of a single Z or E isomer of the compound (II); a composition comprising a single enantiomer or diastereoisomer of a single Z or E isomer of the compound (III); a composition comprising a single enantiomer or diastereoisomer of the compound (IV); a composition comprising a single enantiomer or diastereoisomer of the compound (V); a composition comprising a single enantiomer or diastereoisomer of the compound (VIII); a composition comprising a single enantiomer or diastereoisomer of the compound (IX).

The compounds of the invention may be prepared by many methods which are known to a person skilled in the art, the invention in particular also provides a process for preparing the compounds of the invention by a Knoevenagel condensation[2]) between a ketone, more particularly 4,6-dimethyl-2-heptanone, and cyanoacetic acid or esters thereof; preferably, this condensation is followed by decarboxylations, as shown, for illustration only, in scheme A. It will be appreciated that scheme A represents a process for synthesis of compounds of the invention in which R is a hydrogen atom.

4,6-Dimethyl-2-heptanone is readily accessible, for example, from by-products of the alkaline ketolization of acetone on the industrial scale[3]). Three positional isomers, of which two may be cis or trans, or a mixture thereof, may be obtained in the condensation, said isomers differing from one another in the relative position of the nitrile group and of the carbon-carbon double bond produced, and also in the geometry around said double bond (α, β: E and Z isomers; β, γ: E and Z isomers; β: methylene).

The amounts of the different isomers obtained in a mixture may vary as a function of the operating conditions[2]). Thus, conventionally, increasing the time and the temperature of the decarboxylation step raises the level of conjugated isomers (II), whereas reducing the amount of basic catalysts promotes the formation of the unsaturated β and γ isomers (III E and Z, IV). The compounds (III) and (IV) may be separated from the mixture by distillation in the presence of a strong acid, whereas treatment in the presence of alcoholic potassium hydroxide allows isolation of the unsaturated α and β isomers in pure form (II).

Scheme A

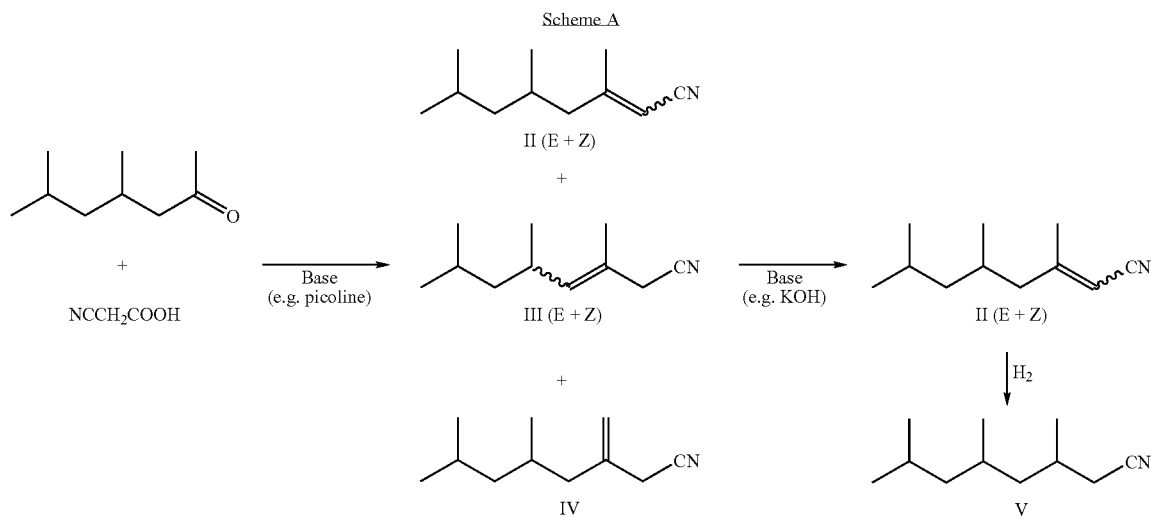

The reduction, by means for example of catalytic hydrogenation at standard temperature and pressure, of the isomers (II), called Verbetryle™, on palladium-on-carbon leads to the saturated nitrile (V) with a yield of 88%. The compound (V) is called Dihydroverbetryle™ (scheme A).

The compounds according to the invention are all characterized by an intense "hesperidium, green" olfactory note, with each of them having specific qualities: the mixture of the isomers II, III, and IV in proportions of 30(II):70(III+IV) exhibits a fruity (pear) note, whereas Verbetryle™, obtained by treating the aforementioned mixture with a base, is characterized more by slightly minty, floral, iris aspects.

Dihydroverbetryle™ (V) rounds out its olfactory palette with floral, aldehydic notes that are reminiscent of geranonitrile. A touch of mint is also perceptible.

Replacing cyanoacetic acid by its ethyl ester in the Knoevenagel condensation gives the unsaturated nitrile ester (VI) (Scheme B). Reducing this nitrile ester, using, for example, sodium borohydride, gives the β-hydroxy nitrile (VII). The latter can be developed to the α,β-unsaturated nitrile (VIII), which gives rise to the nitrile (IX) by hydrogenation under the same conditions as above.

The unsaturated nitrile (VIII) is characterized by "mandarin essence, floral" notes, whereas its saturated homolog (IX) exhibits "lactone, fruity and sweet almond" notes.

The compounds according to the invention are raw materials of olfactory intensity and can therefore find use for providing, boosting or enhancing the fragrance of a wide variety of products.

The invention, therefore, additionally provides for the use of at least one compound of formula (I) according to the invention as an odorant agent, as an odor masking agent or as an odor neutralizing agent, alone or in a mixture with one or more other odorant compounds known to a person skilled in the art, and which a person skilled in the art is capable of selecting as a function of the desired effect. The additional odorant agent or agents may be compounds of formula (I) or other odorant agents known to a person skilled in the art.

For the purposes of the present invention, the term "perfumery" denotes not only perfumery in the common sense of the term, but also the other fields in which the odor of products is important. The compounds of the invention may form part of perfumery compositions in the usual sense of the term, such as perfuming bases and concentrates, eau de cologne, Scheme B

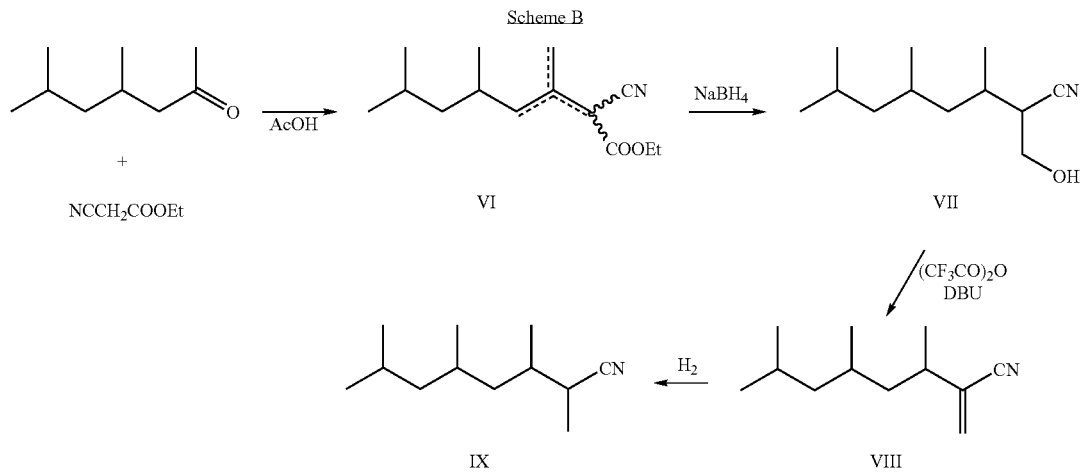

eau de toilette, perfumes, and similar products; topical compositions—especially topical cosmetic compositions—such as creams for the face and the body, talcum powders, body hygiene products, especially shampoos, cleansing products for the body and hair, oils for hair, body lotions, bath salts and oils, bath and shower gels, toilet soaps, body antiperspirants and deodorants, shaving or after-shave lotions and creams, creams, dentifrices, mouthwashes, pomades, and similar products; and household products, such as softeners, fabric softeners, detergents, laundering products, room deodorizers, home maintenance and disinfectant products, and similar products.

The compounds of the invention are therefore odorant compounds which can be used in perfumery, and more particularly as constituents of a perfume. In the context of this invention, a perfume is a mixture of odorant substances which can dissolved or mixed with a solid vehicle in order to impart the desired odor to the skin or to any other substrate for which a pleasant odor is necessary or desirable. The term odorant is used here to refer to a compound which emits an odor.

The invention accordingly provides a perfumery composition, more particularly a perfuming concentrate or base, eau de cologne, eau de toilette or perfume, characterized in that it comprises at least one compound according to the invention. The invention provides in particular a cosmetic composition, more particularly a cream for the face and body, talcum powder, oil for hair or for the body, shampoo, hair lotion, bath salt, bath oil, shower gel, bath gel, toilet soap, body antiperspirant, body deodorant, lotions, shaving cream, shaving soap, cream, dentifrice, mouthwash or pomade, characterized in that it comprises at least one compound according to the invention. The invention likewise provides a household product, more particularly a softener, detergent, laundering product or room deodorizer, characterized in that it comprises at least one compound according to the invention. The invention further provides a preventive or nonpreventive method of cosmetic treatment or care that employs at least one compound of formula (I) or at least one composition comprising at least one compound of formula (I).

The invention also relates to compositions comprising at least one compound of the invention and at least one other odorant substance, selected more particularly from natural products, encompassing essential oils, absolutes, resinoids, concretes, etc., but also synthetic products, such as aliphatic, aromatic or heterocyclic hydrocarbons, alcohols, aldehydes, ketones, ethers, esters, acetals, and nitriles.

The compounds of the invention can be used in perfumery, more particularly in perfumes or perfumed compositions, across a very wide concentration range, which will depend not only on the nature of the end product but also on the concentration of the other ingredients of the composition.

The compounds according to the invention will be present in the perfuming compositions or the perfumes at a concentration, preferably, of at least 0.001% by weight, relative to the total weight of the composition: at this concentration, its odor is perceptible. The compounds according to the invention will be present in the perfuming compositions or perfumes, preferably, at a concentration of at least 0.01% by weight, relative to the total weight of the composition. The compounds according to the invention will be present in the perfumes advantageously in an amount of at least 1 ppm by weight, and preferably 10 ppm.

The invention also relates to the use of at least one compound according to the invention as an odorant agent or as an odor masking agent or as an odor neutralizing agent, optionally in combination with other odorant agents.

The examples which follow endeavor to present, by way solely of illustration, the preparation and use of the compounds of the invention; the invention is by no means limited to said examples.

EXAMPLE 1

Synthesis 1.1 Preparation of the Mixture of 3,5,7-trimethyloctenenitriles of Formulae (II), (III), and (IV) in which R is a Hydrogen Atom The reaction is carried out in a 2-liter three-neck round-bottom flask fitted with an immersed thermometer, with an ascending condenser equipped with a phase separator, and with a 500-milliliter pressure-equalizing dropping funnel.

The flask is charged in succession with 10 g of ammonium acetate (0.13 mol), 20.4 g of 2-picoline (0.22 mol), 160 g of toluene, and 568 g of 4,6-dimethyl-2-heptanone (4 mol). The mixture is taken to total reflux, and the water which separates out is removed as it forms.

A solution of 170 g of cyanoacetic acid (2 mol) in 70 g of clear water (70% solution by mass) is poured into the dropping funnel. This solution is added to the flask at a uniform rate over 12 hours. Foams are formed owing to the elimination of water and of carbon dioxide. The water is removed regularly from the phase separator. The total reflux is maintained for 6 hours after the end of addition, and then the absence of evolution of carbon dioxide is verified. When the distillate is clear, it is collected in a receiver and set aside. Operation is interrupted when a temperature of 145-150° C. is obtained in the vapors. Heating is interrupted, and a conventional distillation assembly is substituted for the phase separator. A liquid ring pump is connected to the resultant assembly, and then the vacuum is decreased very gradually. The second distillate is collected progressively until a vapor temperature of 60-65° C. under 18 torr is reached. This is the excess ketone introduced.

The residue is washed with saturated aqueous sodium bicarbonate solution and dried and is then distilled (b.p.=87-95° C./5 torr). 210 g of nitrile are collected, which represents a yield of 63.5%.

The proportion of the conjugated (E+Z) isomers (II) relative to the nonconjugated isomers (III) and (IV) (see scheme A) was established by integrating specific signals in the proton NMR (signals alpha to the nitrile): for the isomers (II), the vinyl proton is situated at 5.0 ppm for one isomer and at 5.18 ppm for the other; the protons located α to the nitrile group are situated at 3.05 ppm for the isomers (III) and (IV) for which R is a hydrogen atom.

Accordingly it is possible to work out that the isomers (I) represent 30% of the mixture.

1.2 Preparation of 3,5,7-trimethyl-2-octenenitrile of the Formula II in which R is a Hydrogen Atom: (Verbetryle™)

A 500 ml round-bottom flask is charged in succession with 100 g of ethanol, 16.56 g of potassium hydroxide (0.295 mol) and then 210 g of nitrile for equilibration (1.27 mol). The mixture is stirred at ambient temperature for 16 hours and then cooled to between 0 and 5° C. 85% phosphoric acid (54.4 g) is added slowly, the pH is checked (it should be approximately 7), and then the ethanol is distilled off under reduced pressure.

The residue is rectified under vacuum through a short column and then it is distilled under vacuum (b.p.=85-90° C./5 torr). The distilled product weighs 196 g, corresponding to a yield of 93.3%. This product is a mixture of 2 E:Z isomers in respective proportions of 60:40 (Gas Chromatography). It is obtained in the form of a colorless liquid which has a very characteristic odor.

1) IR: 3051, 2956, 2218, 1629, 1459, 1385, 1367, 829, 806, 791 cm$^{-1}$

2) MS (70 eV): m/e=165(M+•), 164, 151, 150, 122, 108, 85, 81, 69 amu

3) $^1$H NMR: CDCl$_3$; 200 MHz:

δ (ppm): 0.80 to 0.90 (m, 9H); 1.04 (d*d, 7.0/7.0 Hz, 2H); 1.12 (d*d, 7.3/7.3 Hz, 2H); 1.50 to 2.00 (m, 4H); 1.92 (d, 1.6 Hz, 3H); 2.02 (d, 1.0 Hz, 3H); 2.10 to 2.40 (m, 4H); 5.10 (m, 1H); 5.18 (m, 1H)

The underlined signals relate to the minority isomer.

4) $^{13}$C NMR: CDCl$_3$; 50 MHz:

δ (ppm): 19.3; 19.4; 20.8; 22.0; 22.1; 23.0; 23.3; 23.5; 25.1; 44.1; 46.2; 46.3; 46.9; 96.3; 96.7; 117.2; 164.5; 164.6

1.3 Preparation of the 3,5,7-trimethyloctane nitrile (V): (Dihydroverbetryle)

A 250 ml autoclave is charged in succession with 16.5 g of Verbetryle (II), 2 g of palladium on carbon (5%), and then 150 ml of dry toluene. The resulting solution is stirred for 24 hours under 1 atmosphere of hydrogen, filtered and then washed with 5N hydrochloric acid solution. The resulting product is distilled under vacuum (b.p.=92-95° C./6 torr), to give 15 g of nitrile V.

The yield is 90%.

1) IR: 2249, 1460, 1420, 1386, 1368 cm$^{-1}$

2) MS (70 eV): m/e=167(M+•), 166, 152, 124, 110(100), 96, 85, 69 amu

3) $^1$H NMR: CDCl$_3$; 200 MHz: Mixture of 4 diastereoisomers.

δ (ppm): 0.8 to 0.9 (m, 3H); 1.0 to 1.1 (m, 3H); 1.10 to 2.00 (m, 7H); 2.20 to 2.35 (m, 2H)

4) $^{13}$C NMR: CDCl$_3$; 50 MHz:

δ (ppm): 17.2; 17.5; 18.1; 18.2; 20.2; 20.4; 21.4; 21.6; 22.4; 23.1; 23.2; 23.4; 25.7; 25.8; 25.9; 26.0; 41.9; 42.0; 44.6; 45.2; 94.8; 116.9; 117.0.

1.4 Preparation of 2-carboethoxy-3,5,7-trimethyl-2-octenenitrile (VI)

A 250 ml round-bottom flask equipped with a Dean-Stark apparatus is charged in succession with 25.6 g of 4,6-dimethylheptanone (0.18 mol), 14.34 g of ethyl cyanoacetate (0.127 mol), 1.95 g of ammonium acetate, 6 g of acetic acid, and 100 ml of methylcyclohexane. The mixture is heated to reflux, the water formed being separated off as it is formed. After one hour, the mixture is cooled to ambient temperature and then washed to neutrality with saturated sodium bicarbonate solution. The residue is distilled under vacuum (6 torr) for recovery of the excess ketone (6.5 g) and then under a high vacuum for isolation of the cyano ester VI. 25.8 g of a colorless liquid are collected (b.p.=100-104° C./2.10−1 torr), corresponding to a yield of 85%.

Examination of the proton NMR spectrum (see below) shows the absence of vinylic proton and hence of deconjugated derivatives. Integration of the signals for the methyl radicals carried by the carbon-carbon double bond (2.28 ppm for the minority isomer, 2.36 for the majority isomer) shows the presence of two E/Z isomers in proportions of 40/60.

1) IR: 2224, 1731, 1603, 1465, 1368, 1287, 1228, 1099, 1070, 858, 777 cm$^{-1}$

2) MS (70 eV): m/e=237(M+•), 222, 192, 180, 164, 153, 135, 125, 97, 85(100), 69 amu 3) $^1$H NMR: CDCl$_3$; 200 MHz: The underlined signals correspond to the minority isomer.

δ (ppm): 0.8 to 1.0 (m, 9H), 1.0 to 1.3 (m, 2H), 1.34 (t, J=7.2 Hz, 3H), 1.35 (t, J=7.2 Hz, 3H), 1.5 to 2.1 (m, 2H), 2.28 (s, 3H), 2.36 (s, 3H), 2.48 (m, 1H), 2.76 (m, 1H), 4.27 (q., J=7.2 Hz, 2H), 4.28 (q., J=7.2 Hz, 2H)

4) $^1$H NMR: CDCl$_3$; 200 MHz: The underlined signals correspond to the minority isomer.

δ (ppm): 14.8; 19.7; 21.6; 22.4; 23.6; 23.7; 25.5; 25.7; 30.4; 30.9; 42.6; 46.7; 46.9; 48.6; 62.0; 106.0; 106.4; 116.3; 162.1; 162.4; 177.0; 177.1.

1.5 Preparation of 2-hydroxymethyl-3,5,7-trimethyloctanenitrile (VII)

The reaction is carried out in a 1 l three-neck round-bottom flask equipped with an ascending condenser, an immersed thermometer, and a 250 ml pressure-equalizing dropping funnel. The flask is charged in succession with 11.4 g (0.3 mol) of sodium borohydride and then 300 ml of absolute ethanol cooled to 0° C. The dropping funnel is charged with a solution of 47.4 g (0.2 mol) of cyano ester (VI) in 100 ml of absolute ethanol. The contents of the flask are cooled to −15° C., and then the contents of the funnel are added, without 0° C. being exceeded. The resultant mixture is stirred at ambient temperature for 16 hours and then treated in succession with 50 ml of acetone and 200 ml of 5N hydrochloric acid. The mixture is stirred for 5 hours and then the ethanol is removed by distillation. The residue is extracted with 3 times 200 ml of methyl tert-butyl ether. The organic phases are concentrated and then distilled under a high vacuum. A colorless liquid is obtained (30.7 g) (b.p.=100-102° C./2.10$^{-1}$ torr), representing a yield of 78%.

1) IR: 3460, 2244, 1465, 1385, 1367, 1166, 1062, 1028, 573 cm$^{-1}$

2) MS (70 eV): m/e=197(M+•), 182, 152, 141, 140, 124, 110, 85, 68, 43(100) amu

3) $^1$H NMR: CDCl$_3$; 200 MHz: Mixture of 4 diastereoisomers

δ (ppm): 0.8 to 0.9 (m, 3H); 1.0 to 1.1 (m, 3H); 1.10 to 2.00 (m, 7H); 2.60 to 2.90 (m, 1H); 3.50 (s, 1H); 3.60 to 4.00 (m, 2H)

4) $^{13}$C NMR: CDCl$_3$; 50 MHz: Mixture of 4 diastereoisomers

δ (ppm): 13.6; 14.3; 15.5; 15.9; 16.9; 17.2; 17.9; 18.6; 19.5; 20.0; 20.2; 20.4; 20.9; 21.2; 21.4; 22.0; 22.9; 23.0; 23.1; 25.2; 25.3; 25.4; 25.6; 26.7; 26.9; 27.4; 27.5; 38.1; 38.4; 39.5; 39.6; 39.7; 40.1; 41.0; 41.2; 43.3; 44.3; 45.1; 45.6; 58.4; 58.5; 59.0; 59.2; 117.7; 117.9; 118.5; 118.6.

1.6 Preparation of 2-methylene-3,5,7-trimethyloctanenitrile (VIII)

A 250 ml three-neck round-bottom flask which is dry and is purged with nitrogen is charged in succession with 19.7 g of the cyano alcohol (VII) (0.1 mol), 150 ml of anhydrous methylene chloride, and then 18.26 g (0.11 mol) of DBU (1,8-diazabicyclo[5.4.0]undec-7-ene). The solution is cooled to 0° C. and then 22.05 g (0.105 mol) of trifluoroacetic anhydride are added dropwise, without 5° C. being exceeded in the mass. The resulting solution is stirred at ambient temperature for 16 hours and then hydrolyzed, dried, and concentrated.

The residue is distilled under vacuum (6 torr) to give 16 g of unsaturated nitrile (VIII), which distills at 105-108° C. The yield is 89%.

1) IR: 2222, 1622, 1460, 1383, 935, 651 cm$^{-1}$
2) MS (70 eV): m/e=179(M+•), 178, 164, 136, 122, 108, 95, 83, 57(100) amu
3) $^1$H NMR: CDCl$_3$; 200 MHz: Mixture of 2 diastereoisomers δ (ppm): 0.8 to 0.9 (m, 3H); 1.00 to 1.80 (m, 9H); 2.5 (m, 1H); 5.70 (s, 1H); 5.80 (d, J=2 Hz, 1H)

4) $^{13}$C NMR: CDCl$_3$; 50 MHz:

δ (ppm): 19.6; 19.9; 20.2; 20.7; 22.5; 22.8; 23.6; 24.0; 25.4; 25.5; 37.1; 37.4; 43.0; 43.3; 46.9; 47.3; 118.0; 118.2; 128.8; 129.2; 129.4; 130.0.

1.7 Preparation of 2,3,5,7-tetramethyloctanenitrile (IX):

A 250 ml autoclave is charged in succession with 15 g of nitrile VIII, 2 g of palladium on carbon (5%), and 100 ml of dry toluene. The mixture is stirred under one standard pressure of hydrogen. The progress of the reaction is monitored by gas chromatography. When the reaction is at an end, the reaction mixture is filtered, washed with 5N hydrochloric acid solution, and then concentrated. The residue is distilled under vacuum to give 13.65 g of a colorless liquid, representing a yield of 90%. b.p.=100-102° C./6 torr 1) IR: 2239, 2212, 1465, 1385, 1368, 1168 cm$^{-1}$
2) MS (70 eV): m/e=181(M+•), 180, 166, 138, 125, 124, 110, 85, 71, 55, 43(100) amu
3) $^1$H NMR: CDCl$_3$; 200 MHz: Mixture of 4 diastereoisomers δ (ppm): 0.8 to 0.9 (m, 3H); 1.10 to 1.90 (m, 1H); 2.60 (m, 1H)

4) $^{13}$C NMR: CDCl$_3$; 50 MHz: Mixture of 4 diastereoisomers

δ (ppm): 14.5; 15.3; 15.6; 16.2; 16.4; 17.4; 17.6; 19.5; 19.7; 20.5; 20.9; 22.1; 22.4; 22.8; 23.4; 23.6; 23.9; 24.2; 25.4; 25.5; 25.6; 27.8; 27.9; 28.0; 31.0; 31.5; 32.2; 32.3; 33.5; 33.8; 33.9; 40.8; 41.6; 43.1; 43.6; 46.2; 46.7; 47.7; 48.0; 122.0; 122.3; 122.7; 122.9.

EXAMPLE 2

Olfactory evaluation of Verbetryle (II) and of Dihydroverbetryle™ (V) in a Perfuming Composition Olfactory description:

Verbetryle (II): green, hesperidium, iris, floral, slightly mint.

Dihydroverbetryle™ (V): green, natural grapefruit, slightly mint.

Perfuming compositions were created (tests 2 and 3) in which the olfactory impact of Verbetryle™ and of Dihydroverbetryle™ was examined by comparison with a composition not containing the compound (test 1).

| Components | Test 1 (weight) | Test 2 (weight) | Test 3 (weight) |
|---|---|---|---|
| Bergamot composition | 100.00 | 100.00 | 100.00 |
| Caraway essence | 10.00 | 10.00 | 10.00 |
| Lemon terpenes | 100.00 | 100.00 | 100.00 |
| Metra mouse de Metra | 10.00 | 10.00 | 10.00 |
| Coumarin | 10.00 | 10.00 | 10.00 |
| Methyl-chavicol | 10.00 | 10.00 | 10.00 |
| Eugenol | 10.00 | 10.00 | 10.00 |
| Galaxolide | 55.00 | 55.00 | 55.00 |
| Lavender essence | 25.00 | 25.00 | 25.00 |
| Lavandin essence | 20.00 | 20.00 | 20.00 |
| USA peppermint essence | 15.00 | 15.00 | 15.00 |
| Methyl dihydrojasmonate | 70.00 | 70.00 | 70.00 |
| Neroli composition | 100.00 | 100.00 | 100.00 |
| Octahydrotetramethylacetonaphthone | 100.00 | 100.00 | 100.00 |
| Orange essence | 200.00 | 200.00 | 200.00 |
| Spearmint essence | 55.00 | 55.00 | 55.00 |
| Mandarin composition | 10.00 | 10.00 | 10.00 |
| Dipropylene glycol | 100 | 70 | 70 |
| Verbetryle ™ | 0 | 30 | 0 |
| Dihydroverbetryle ™ | 0 | 0 | 30 |

These compositions were tested, for example, in a pearlized shower gel base, at a proportion of 0.5% by weight. The composition of test 2 imparts a masculine aromatic peppermint note, while the composition of test 3 imparts a natural grapefruit note with a slight touch of bitterness relative to the composition of test 1.

REFERENCES

1) M. Erman; Advances in the Chemistry of Nitriles and Amides; Perfumer and Flavorist, 27, 30, (2002).
2) G. Jones; The Knoevenagel Condensation; Organic Reactions 15, 204, (1967) John Wiley and Sons Ed.; New York, London, Sydney.
3) A. Hinnen and J. Dreux; Bull. Soc. Chim. Fr., 1964, p. 1492.

The invention claimed is:

1. Compounds of general formula (I) below:

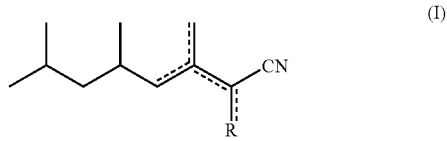

(I)

in which R is a hydrogen atom, a methyl group or a methylene group and in which not more than one of the four dashed lines represents a carbon-carbon double bond, and their enantiomers and their diastereoisomers.

2. The compounds as claimed in claim 1, of general formula (II) below:

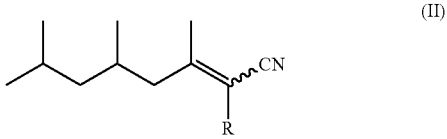

(II)

in which R is a hydrogen atom or a methyl group, their Z or E isomers, and their enantiomers.

3. The compounds as claimed in claim 1, of general formula (III) below:

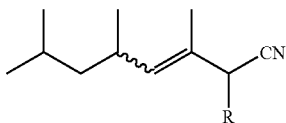

(III)

in which R is a hydrogen atom or a methyl group, their Z or E isomers, their enantiomers, and their diastereoisomers.

4. The compounds as claimed in claim 1, of general formula (IV) below:

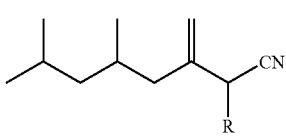

(IV)

in which R is a hydrogen atom or a methyl group, their enantiomers, and their diastereoisomers.

5. The compounds as claimed in claim 1, of general formula (V) below:

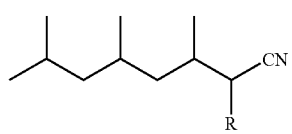

(V)

in which R is a hydrogen atom or a methyl group, their enantiomers, and their diastereoisomers.

6. The compound as claimed in claim 1, of general formula (VIII) below:

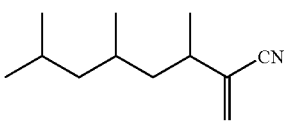

(VIII)

its enantiomers, and its diastereoisomers.

7. A composition characterized in that it comprises at least one compound as defined in claim 1 in the form of an isomer or mixture of isomers, an enantiomer or mixture of enantiomers, or a racemic mixture, or a diastereoisomer or mixture of diastereoisomers.

8. The composition as claimed in claim 7, comprising a mixture of formulas (II), (III), and (IV).

9. The composition as claimed in claim 7, comprising at least one of the two Z and E isomers of formula (II), or a mixture of said two isomers.

10. The composition as claimed in claim 7, comprising at least one of the four diastereoisomers of formula (V), or a mixture of said four diastereoisomers.

11. The composition as claimed in claim 7, comprising at least one compound selected from the group of formulas (I), (II), (III), (IV), (V) and (VIII) and at least one other odorant substance.

12. A method of providing an odor to a composition, product or product base comprising adding the composition as claimed in claim 7 as an odorant agent or odor masking agent or odor neutralizing agent to said composition, product or product base, optionally in combination with other odorant agents.

13. A perfumery composition comprising at least one compound as defined in claim 1 or a compound as claimed in claim 1 in the form of an isomer or mixture of isomers, an enantiomer or mixture of enantiomers, or a racemic mixture, or a diastereoisomer or mixture of diastereoisomers, and a perfuming concentrate or base, eau de cologne, eau de toilette or perfume.

14. A cosmetic composition, comprising at least one compound as defined in claim 1 or a compound as claimed in claim 1 in the form of an isomer or mixture of isomers, an enantiomer or mixture of enantiomers, or a racemic mixture, or a diastereoisomer or mixture of diastereoisomers, and a cream for the face and the body, talcum powder, oil for hair or for the body, shampoo, hair lotion, bath salt, bath oil, shower gel, bath gel, toilet soap, body antiperspirant, body deodorant, lotions, shaving cream, shaving soap, cream, dentifrice, mouthwash or pomade.

15. A household product comprising at least one compound as defined in claim 1 or a compound as claimed in claim 1 in the form of an isomer or mixture of isomers, an enantiomer or mixture of enantiomers, or a racemic mixture, or a diastereoisomer or mixture of diastereoisomers, and a softener, detergent, laundering product or room deodorizer.

16. A method of providing an odor to a composition, product or product base comprising adding at least one compound of formula (I) as defined in claim 1 or of a compound as claimed in claim 1 in the form of an isomer or mixture of isomers, an enantiomer or mixture of enantiomers, or a racemic mixture, or a diastereoisomer or mixture of diastereoisomers as an odorant agent or odor masking agent or odor neutralizing agent to said composition, product or product base, optionally in combination with other odorant agents.

17. A process for preparing the compounds of formula (I) as described in claim 1, wherein a ketone and cyanoacetic acid or an ester thereof are subjected to a Knoevenagel condensation.

18. The process as claimed in claim 17 wherein the ketone is 4,6-dimethyl-2-heptanone.

* * * * *